US010916335B1

(12) United States Patent
Chugh et al.

(10) Patent No.: US 10,916,335 B1
(45) Date of Patent: Feb. 9, 2021

(54) HASHHEALTH SYSTEM

(71) Applicant: ALLSCRIPTS SOFTWARE, LLC, Chicago, IL (US)

(72) Inventors: Manish Chugh, Pune (IN); Avnish Verma, Pune (IN); Manish Singh, Pune (IN)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 663 days.

(21) Appl. No.: 15/157,488

(22) Filed: May 18, 2016

(51) Int. Cl.
| | |
|---|---|
| *G16H 10/60* | (2018.01) |
| *G06Q 50/00* | (2012.01) |
| *G06F 19/00* | (2018.01) |
| *H04L 29/06* | (2006.01) |
| *G06Q 30/04* | (2012.01) |

(52) U.S. Cl.
CPC .......... *G16H 10/60* (2018.01); *G06F 19/324* (2013.01); *G06Q 30/04* (2013.01); *G06Q 50/01* (2013.01); *H04L 63/08* (2013.01); *H04L 63/102* (2013.01)

(58) Field of Classification Search
USPC ........................................................ 705/2, 3
See application file for complete search history.

(56) References Cited

U.S. PATENT DOCUMENTS

| | | | | |
|---|---|---|---|---|
| 2008/0319794 | A1* | 12/2008 | Carlson | G06Q 20/3255 705/3 |
| 2014/0081809 | A1* | 3/2014 | King | G06Q 20/405 705/26.82 |
| 2016/0330770 | A1* | 11/2016 | Lee | H04W 4/025 |
| 2017/0024721 | A1* | 1/2017 | Joson | G06Q 20/322 |

OTHER PUBLICATIONS

Michelle Swab and Kristen Romme, "Scholarly Sharing via Twitter: #icanhazpdf Requests for Health Sciences Literature", JCHLA / JABSC 37: 611 (2016). (Year: 2016).*

* cited by examiner

*Primary Examiner* — Aryan E Weisenfeld
*Assistant Examiner* — Joshua B Blanchette
(74) *Attorney, Agent, or Firm* — Medley, Behrens & Lewis, LLC

(57) ABSTRACT

A method includes receiving, at a healthcare platform, account registration information from a user submitted via a mobile application; receiving, at the healthcare platform, an indication of a social media account to link to the user's account; receiving, at a social media interface of the healthcare platform, a message posted by the user via the social media account which includes a command comprising a command identifier; forwarding, based on the presence of the command comprising the command identifier, the command to a command handler of the healthcare platform; retrieving, by the healthcare platform, healthcare information for the user based on the command; and communicating, by the healthcare platform, the retrieved information via text message to a cell phone number associated with the user's account.

20 Claims, 1 Drawing Sheet

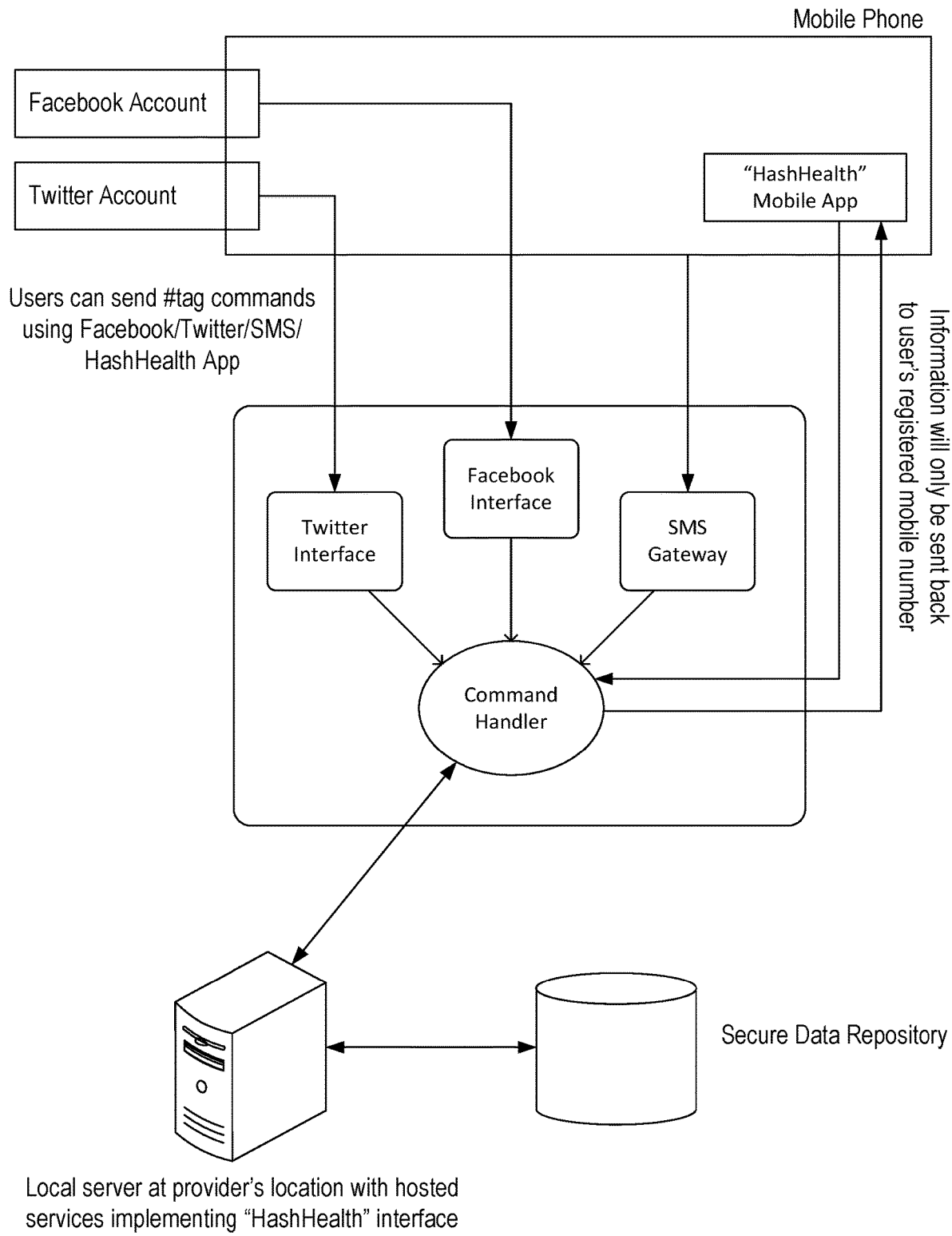

HASHHEALTH SYSTEM

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to healthcare information exchange.

Currently, there are a limited number of ways for a patient to obtain information from a healthcare provider. A patient can visit a healthcare provider in person, but this can be very time consuming, and no one may be available to help when the patient arrives. A patient can call or email, but this can still be very time consuming for both the patient and any personnel tasked with responding to the communication. Some healthcare providers provide a website or portal which allows for access to health information, but this requires registering and remembering authentication credentials for the website or portal, and may still not provide the information the patient seeks.

A need exists for improvement in healthcare information exchange. This, and other needs, are addressed by one or more aspects of the present invention.

SUMMARY OF THE INVENTION

The present invention includes many aspects and features. Moreover, while many aspects and features relate to, and are described in a particular context, the present invention is not limited to use only in this context, as will become apparent from the following summaries and detailed descriptions of aspects, features, and one or more embodiments of the present invention.

Accordingly, one aspect of the present invention relates to a method comprising receiving, at a healthcare platform, account registration information from a user submitted via a mobile application; receiving, at the healthcare platform, an indication of a social media account to link to the user's account; receiving, at a social media interface of the healthcare platform, a message posted by the user via the social media account which includes a command comprising a command identifier; forwarding, based on the presence of the command comprising the command identifier, the command to a command handler of the healthcare platform; retrieving, by the healthcare platform, healthcare information for the user based on the command; and communicating, by the healthcare platform, the retrieved information via text message to a cell phone number associated with the user's account.

In a feature of this aspect, the social media platform comprises Facebook.

In a feature of this aspect, the social media platform comprises Twitter.

In a feature of this aspect, the command identifier comprises a hashtag.

In a feature of this aspect, the command comprises a request for billing information.

In a feature of this aspect, the command comprises a request for patient information.

In a feature of this aspect, the command comprises a request for medication information.

In a feature of this aspect, the command comprises a request for medical history information.

In a feature of this aspect, the command comprise a request for allergy information.

In a feature of this aspect, the command comprises a request for appointment information.

Another aspect relates to a method comprising receiving, at a healthcare platform, account registration information from a user submitted via a mobile application; receiving, at the healthcare platform, an indication of a cell phone number to link to the user's account; receiving, at a SMS gateway of the healthcare platform, a message sent by the user which includes a command comprising a command identifier; forwarding, based on the presence of the command comprising the command identifier, the command to a command handler of the healthcare platform; retrieving, by the healthcare platform, healthcare information for the user based on the command; and communicating, by the healthcare platform, the retrieved information via text message to the cell phone number associated with the user's account.

Another aspect relates to a method comprising receiving, at a healthcare platform, account registration information from a user submitted via a mobile application; receiving, at the healthcare platform, a request submitted via the mobile application which includes a command comprising a command identifier; forwarding, based on the presence of the command comprising the command identifier, the command to a command handler of the healthcare platform; retrieving, by the healthcare platform, healthcare information for the user based on the command; and communicating, by the healthcare platform, the retrieved information via text message to a cell phone number associated with the user's account.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein:

FIG. 1 illustrates an exemplary system in accordance with one or more preferred implementations.

DETAILED DESCRIPTION

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

In accordance with one or more preferred implementations, a system is configured to allow users (e.g. patients, doctors, and medical staff) to access specific medical information utilizing a social media platform, mobile application, and/or text message.

In accordance with one or more preferred implementations, users can send a specific query for information via one of these communication channels which includes a command identifier indicating the nature of the communication as a specific query. In accordance with one or more preferred implementations, such command identifier is a hashtag, and hashtag commands may be utilized to request specific information associated with such hashtag commands.

In accordance with one or more preferred implementations, registered users of a social media platform such as Facebook can post a # tag command on a provider's page.

In accordance with one or more preferred implementations, registered users of Twitter can tweet a # tag command at a provider.

In accordance with one or more preferred implementations, registered users of a mobile application (e.g. available via an app store) can send a # tag command via the mobile application.

In accordance with one or more preferred implementations, a user can send a # tag command as a text message (e.g. SMS), which preferably could be utilized even in the absence of data connectivity.

In accordance with one or more preferred implementations, a system includes a mobile application (e.g. available for Android and iOS). Preferably, a user can install the app and register with a healthcare provider, and link his or her Facebook or Twitter accounts using settings provided by the mobile app. A registered user will be able to use a set of predefined # tag commands provided within the mobile app. Users can use the same set of commands through Twitter, Facebook, or SMS.

In accordance with one or more preferred implementations, irrespective of the interface used for requesting the information, the system will only respond back on users registered direct cell number (or in the mobile app itself).

In accordance with one or more preferred implementations, sample # tag commands that might be utilized by a patient user include "# HHmed", which could be utilized to obtain current medication information, "# HHalg", which could be utilized to obtain current allergy information, and "# HHapt", which could be utilized to obtain current appointment details.

In accordance with one or more preferred implementations, sample # tag commands that might be utilized by a provider user include "# HHbud2015", which might return a budget amount for a year, and "# HHp&12014", which return a profit and loss statement for a year.

In accordance with one or more preferred implementations, a system provides a pluggable interface, which any health care provider will be able implement using configurable options using published API's. Providers will have the flexibility to create new Hashtags. Preferably, for these new Hashtags, a new method signatures will be generated and added to the programming interface.

In accordance with one or more preferred implementations, providers will have to implement a Restful web service using the programming interface provided by a system. This interface will have a method linked to every # tag command in the repository.

In accordance with one or more preferred implementations, an engine is responsible for handling all the requests from users, redirecting requests to web services and sending back responses (e.g. to a user's registered direct cell phone number).

In accordance with one or more preferred implementations, an engine has a Facebook interface which is programmed to receive # tag commands posted by a registered user using their linked Facebook account. This interface will forward the requests to a command handler.

In accordance with one or more preferred implementations, an engine includes a Twitter interface programmed to receive # tag commands raised through tweets by registered users using their linked Twitter account. This interface will forward the requests to a command handler.

In accordance with one or more preferred implementations, an engine includes an SMS gateway responsible for receiving # tag commands via SMS sent by registered users and forward the request to a command handler.

In accordance with one or more preferred implementations, a command handler will receive commands from social network interfaces and/or an SMS gateway or directly from a mobile app and will map those commands to the appropriate methods and will call those web service methods to request the relevant information. Once it hears back from web service it will redirect the response back to a user's registered direct cell phone number.

FIG. 1 illustrates an exemplary system in accordance with one or more preferred implementations which includes such interfaces and a command handler.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method executed by a healthcare platform, the method comprising:
   receiving account registration information for a user from a mobile application executing on a mobile phone operated by the user, wherein the account registration information includes a phone number of the mobile phone and an identifier of a social media account of the user;
   generating a user account for the user based upon the account registration information, wherein the user account links the account registration information to a patient record of the user;
   responsive to generating the user account, causing a social media interface of the healthcare platform to monitor the social media account of the user for messages posted by the user;
   receiving, at the social media interface of the healthcare platform, a message posted by the user via the social media account of the user, wherein the message includes the identifier of the social media account, a command identifier, and a command, wherein the command identifier indicates that the healthcare platform is to execute the command, wherein the command is indicative of a query that is to be executed by the healthcare platform in order to retrieve healthcare information of the user from the patient record, wherein the command identifier and the command are a sequence of non-space delimited alphanumeric characters;
   forwarding the identifier of the social media account included in the message and the command to a command handler of the healthcare platform;
   identifying, by the command handler of the healthcare platform, the user account based upon the identifier of the social media account included in the message;
   responsive to identifying the user account, retrieving, by the command handler of the healthcare platform, the healthcare information of the user from a secure data repository retaining the patient record by executing the query indicated by the command; and
   transmitting a text message to the phone number of the mobile phone operated by the user, wherein the text message includes the healthcare information of the user.

2. The method of claim 1, wherein the command identifier comprises a hashtag.

3. The method of claim 1, wherein the command comprises a request for billing information.

4. The method of claim 1, wherein the command comprises a request for patient information.

5. The method of claim 1, wherein the command comprises a request for medication information.

6. The method of claim 1, wherein the command comprises a request for medical history information.

7. The method of claim 1, wherein the command comprises a request for allergy information.

8. The method of claim 1, wherein the command comprises a request for appointment information.

9. A server computing device comprising:
   a processor; and
   memory storing instructions that, when executed by the processor, cause the processor to perform acts comprising:
      receiving account registration information for a user from a mobile application executing on a mobile phone operated by the user, wherein the account registration information includes a phone number of the mobile phone and an identifier of a social media account of the user;
      generating a user account for the user based upon the account registration information, wherein the user account links the account registration information to a patient record of the user;
      responsive to generating the user account, causing a social media interface of the healthcare platform to monitor the social media account of the user for messages posted by the user;

receiving, at the social media interface of the healthcare platform, a message posted by the user via the social media account of the user, wherein the message includes the identifier of the social media account, a command identifier, and a command, wherein the command identifier indicates that the healthcare platform is to execute the command, wherein the command is indicative of a query that is to be executed by the healthcare platform in order to retrieve healthcare information of the user from the patient record, wherein the command identifier and the command are a sequence of non-space delimited alphanumeric characters;

forwarding the identifier of the social media account included in the message and the command to a command handler of the healthcare platform;

identifying, by the command handler of the healthcare platform, the user account based upon the identifier of the social media account included in the message;

responsive to identifying the user account, retrieving, by the command handler of the healthcare platform, the healthcare information of the user from a secure data repository retaining the patient record by executing the query indicated by the command; and transmitting a text message to the phone number of the mobile phone operated by the user, wherein the text message includes the healthcare information of the user.

10. The server computing device of claim 9, wherein the command comprises a request for billing information.

11. The server computing device of claim 9, wherein the command comprises a request for patient information.

12. The server computing device of claim 9, wherein the command comprises a request for medication information.

13. The server computing device of claim 9, wherein the command comprises a request for medical history information.

14. The server computing device of claim 9, wherein the command comprises a request for allergy information.

15. The server computing device of claim 9, wherein the command comprises a request for appointment information.

16. A non-transitory computer-readable storage medium comprising instructions that, when executed by a processor, cause the processor to perform acts comprising:

receiving account registration information for a user from a mobile application executing on a mobile phone operated by the user, wherein the account registration information includes a phone number of the mobile phone and an identifier of a social media account of the user;

generating a user account for the user based upon the account registration information, wherein the user account links the account registration information to a patient record of the user;

responsive to generating the user account, causing a social media interface of the healthcare platform to monitor the social media account of the user for messages posted by the user;

receiving, at the social media interface of the healthcare platform, a message posted by the user via the social media account of the user, wherein the message includes the identifier of the social media account, a command identifier, and a command, wherein the command identifier indicates that the healthcare platform is to execute the command, wherein the command is indicative of a query that is to be executed by the healthcare platform in order to retrieve the healthcare information of the user from the patient record, wherein the command identifier and the command are a sequence of non-space delimited alphanumeric characters;

forwarding the identifier of the social media account included in the message and the command to a command handler of the healthcare platform;

identifying, by the command handler of the healthcare platform, the user account based upon the identifier of the social media account included in the message;

responsive to identifying the user account, retrieving, by the command handler of the healthcare platform, the healthcare information of the user from a secure data repository retaining the patient record by executing the query indicated by the command; and transmitting a text message to the phone number of the mobile phone operated by the user, wherein the text message includes the healthcare information of the user.

17. The non-transitory computer-readable storage medium of claim 16, wherein the command comprises a request for patient information.

18. The non-transitory computer-readable storage medium of claim 16, wherein the command comprises a request for medication information.

19. The non-transitory computer-readable storage medium of claim 16, wherein the command comprises a request for allergy information.

20. The non-transitory computer-readable storage medium of claim 16, wherein the command comprises a request for appointment information.

* * * * *